United States Patent [19]

Schiwiora et al.

[11] Patent Number: 4,952,150
[45] Date of Patent: Aug. 28, 1990

[54] ROOT POST

[75] Inventors: Harry Schiwiora; Manfred Stuemke, both of Pforzheim, Fed. Rep. of Germany

[73] Assignee: Degussa Aktiengesellschaft, Frankfurt an Main, Fed. Rep. of Germany

[21] Appl. No.: 280,434

[22] Filed: Dec. 6, 1988

[30] Foreign Application Priority Data

Dec. 10, 1987 [DE] Fed. Rep. of Germany ....... 3741847

[51] Int. Cl.$^5$ ................................................ A61C 5/08
[52] U.S. Cl. ................................................... 433/220
[58] Field of Search ............... 433/220, 221, 173, 174, 433/175, 176, 222.1, 219, 218, 224, 225

[56] References Cited

U.S. PATENT DOCUMENTS

| 822,582 | 6/1906 | Carmichael | 433/220 |
| 1,583,459 | 5/1926 | Hansen | 433/220 |
| 4,362,511 | 12/1982 | Jacklich | 433/220 |

FOREIGN PATENT DOCUMENTS 3643219  6/1988  Fed. Rep. of Germany ...... 433/220

Primary Examiner—Cary E. Stone
Attorney, Agent, or Firm—Beveridge, DeGrandi & Weilacher

[57] ABSTRACT

In dental technology, in order to match root posts to curved root canals, the fixation part consists of a material with mechanical properties, such as ductility and flexural rigidity, that permit topical matching of the fixation part to the curved root canal. For example, the ductility increases from the oral side of the fixation part to the root apex.

8 Claims, 1 Drawing Sheet

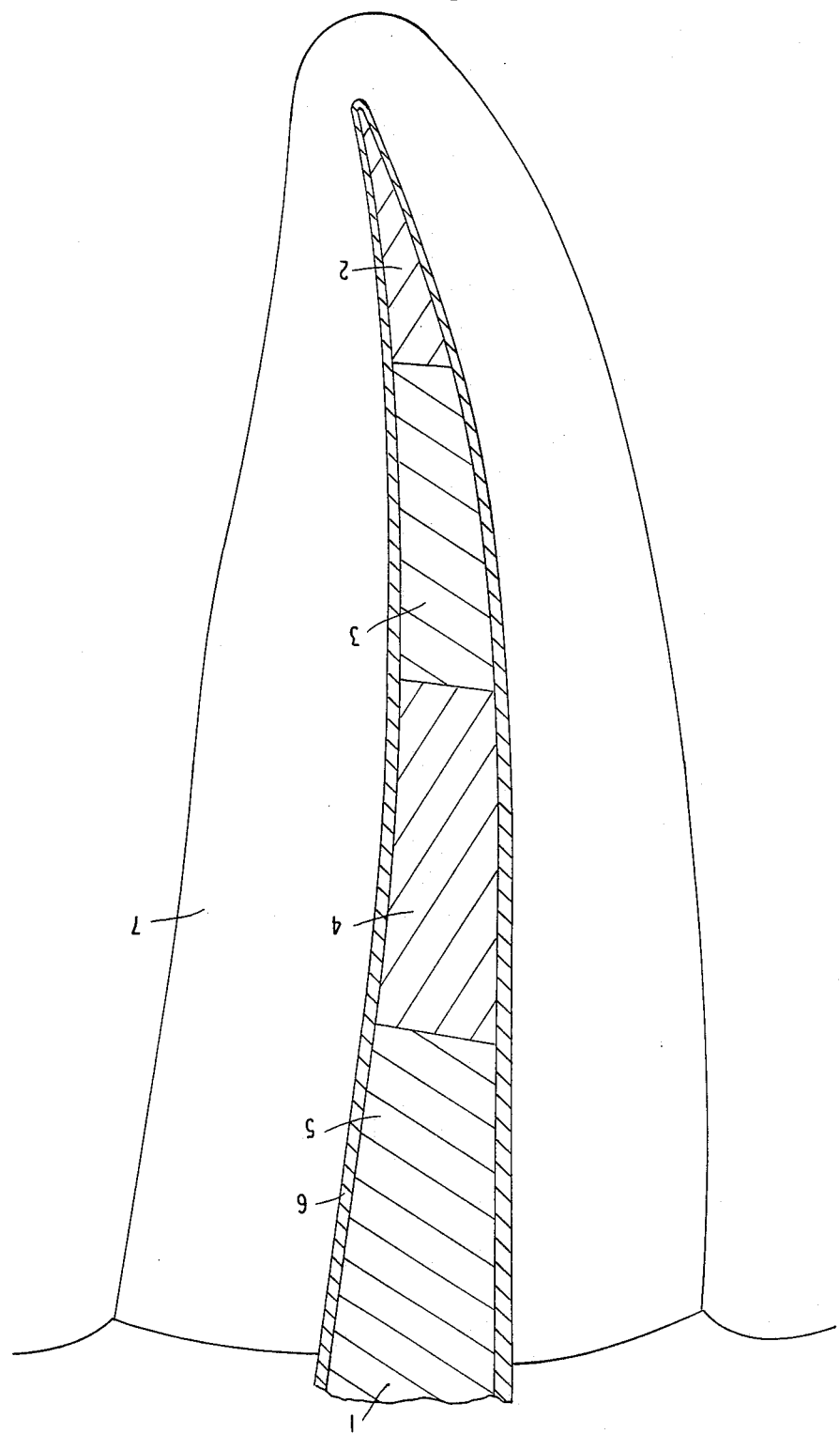

4,952,150

ROOT POST

INTRODUCTION AND BACKGROUND

The present invention relates to a root post with a fixation part made from precious-metal or base-metal alloys that can be inserted into the curved root canal of a dental root.

A natural human tooth consists of a crown and a dental root. The crown, which makes up about ⅓ of the total length of the tooth, projects visibly from the gums into the oral cavity. The conically shaped dental root, about ⅔ of the total length of the tooth, is concealed and fixed in jaw ridge. The nerve of the tooth is embedded in the root from the tip of the root to about the middle of the crown in an axial, conical, curved canal.

In most cases, when the crown is destroyed, e.g., due to caries or trauma, the root, after removal of the nerve, can still be utilized for a prosthetic appliance in order to close the gap between the teeth.

For this purpose, after a well-planned resection of the destroyed crown, the root canal is drilled open with a conical or cylindrical root-canal reamer. Thereafter, by means of a manually operated root-canal trimmer the excavation is brought to a predetermined level that corresponds to the shape and dimensions of a root post to be inserted into the root canal.

Root posts as described for the production of artificial dental structures consist of an elongated, metallic fixation part that serves for the retention in the root, and a head portion mounted at the upper end of the fixation part and on which the new crown is built up. German OLS 35 40 188 shows such a root post.

The fixation or retention part of these root posts is shaped conically or cylindrically and has a smooth surface or is provided with a thread or with structures. As a rule, one uses as materials precious-metal alloys of the AgPd and AuPtPd type and base-metal alloys of the TiAlFe or TiAlv type and CoCrMo.

The root posts are each made of only one material with the identical mechanical properties throughout the length thereof.

All root posts or the fixation parts thereof have a rotationally symmetrical design, since the root-canal reamers and root-canal trimmer too must have conically or cylindrically axially symmetrical shapes and the bores are drilled accordingly in the root canal. The fixation of the posts in the root canals, apart from a certain clamping effect of the post in the canal, is effected via square threads, frictional snug fit, or by cementing them in with phosphate cement.

With roots that have a conical shape and are generally curved, drilling must be effected in a conically or cylindrically axially symmetrical fashion. With these bores, one can at least make allowance for the anatomical conditions of the root and one cannot rule out the danger that during the drilling in a root curvature the root will be perforated. Moreover, a straight fixation part, which in a curved root is partly implanted outside the root canal as well, can transmit the loads non-physiologically from the crown to the residual root, which may lead to possible damage to the periodentium. Peak stresses in the areas of the root in which the fixation part lies outside the root canal are unavoidable in the event of loads, so that the root can be destroyed.

With masticatory loads, the root post is stressed on bending, so that a fixation part that does not abut properly on the wall of the root can be destroyed by alternating bending stresses. The destruction can occur very quickly if upon insertion of the root post with alignment a relatively thick cement layer is produced which can be pulverized if the root post is subject to bending loads on the root post and which clears a fairly large bending path for the post at the oral outlet of the root canal.

After improper guidance of the post at the oral exit of the root canal, all of the masticatory and bending forces are transmitted to the apical zone where the root apex sits relatively securely. In the apical zone, the root post does not usually sit by analogy with the course of the natural root canal and with the taperingly curved root because of the anatomical shapes of the teeth. The root can be subject to rupture in these cases as well.

SUMMARY OF THE INVENTION

Accordingly, an object of the invention resides in the provision of a root post with a fixation part made of precious-metal or base-metal alloys in which implantation of the fixation part outside the root canal can be ruled out.

According to the invention, this and other objects are achieved by providing the material of the fixation part with mechanical properties which permit topical matching of the fixation part to a curved root canal.

Preferably, the material of the fixation part—viewed in the longitudinal direction—has topically differing ductilities or flexural rigidities, with the part located in the tip of the root apex having the greatest ductility or the least flexural rigidity and, toward the oral end of the fixation part, the material—continuously or in sections—is increasingly less ductile or increasingly more flexurally rigid.

BRIEF DESCRIPTION OF THE DRAWING

The invention will be further understood by reference to the drawing which shows a schematic cross-section of a fixation part matched to a curved root.

DETAILED DESCRIPTION OF THE INVENTION

From the viewpoint of root pin manufacture, it is advantageous for the fixation part to consist of several assembled sections that have differing mechanical material properties, with the section in the root apex having the greatest ductility or the least flexural rigidity, and the sections toward the oral end of the fixation part being increasingly less ductile or increasingly more flexurally rigid.

Advantageously, the fixation parts consist of precious-metal alloys that, because of varying composition, thermal and/or mechanical treatment, have—continuously or in sections—differing ductilities or flexural rigidities.

Another advantage results by providing the surface of the fixation part with a layer made of a porous, compressible, biocompatible material. Fine gold or mixtures of fine gold with hydroxyapatite or tricalcium phosphate are especially suitable for this purpose.

The fixation part of the root post embodying the invention may consist of one part or, preferably, depending on the length, of two to four sections. In this case, the sections are made of one or more highly-corrosion-resistant precious-metal alloys of the same alloy system and have differing mechanical properties. For example, the root post is very soft and the subsequent sections are increasingly harder or increasingly less ductile, so that the section at the oral outlet of the root canal has the greatest strength or hardness, as the case may be.

Depending on the various methods used, the individual sections can be bonded together by soldering, welding or sintering.

Because of the differing mechanical properties, espe- (5) at the oral end is the least ductile, and the properties of the other sections (3, 4) lie between the two values.

The following examples illustrate the material composition of a number of root posts of the invention as well as their mechanical properties: Vickers hardness, 0.2% yield point and elongation at break, which can be looked upon as a measure of the ductility:

| | Part of Post | Material | Vickers hardness H V | | 0.2% Yield point N/mm | | Elongation at break % | |
|---|---|---|---|---|---|---|---|---|
| | | | w | a | w | a | w | a |
| Example 1 | 1 | Au | 25 | | 25 | | 40–50 | |
| | 2 | Degulor i (Au78Ag14Pt6,9PdIr0.1) | 60 | | 80 | | 40 | |
| | 3 | Permador (Au60Pt24,9Pd15Ir0.1) | 145 | 230 | 430 | 720 | 15 | 10 |
| Example 2 | 1 | Au Pt Pd | 50 | | 80 | | 40 | |
| | 2 | Au Pt Pd | 100 | | 250 | | 28 | |
| | 3 | Au Pt Pd | 160 | | 460 | | 16 | |
| | 4 | Au Pt Pd | 260 | | 800 | | 10 | |
| Example 3 | 1 | Ti 99.8 | 120 | | 250 | | 22 | |
| | 2 | Ti Al Fe | 250–280 | | 895 | | 16 | | cially because of the differing ductilities within the fixation part, the root post is deformable and, during assembly, can be set in such a way, in accordance with the course of the curved root canal, with an instrument that can release predetermined pulses, that at each point it is matched to the course of the root canal.

Preferably, the surface of the root post is provided with a porous, compressible layer made of a biocompatible, bioinert or bioactive material, particularly with fine gold or mixtures of fine gold with hydroxyapatite, tricalcium phosphate or similar ceramic compounds. The coating is deposited by known methods, e.g., plasma injection, sintering or electrophoresis. This layer has the property of condensing by plastic deformation when the post is being inserted under a predetermined pressure, thereby establishing a very intimate contact with the walls of the root canal. The force required for the deformation of the porous layer must be only a fraction of the force that would be needed to cause the root to rupture.

With the root post incorporating the invention, one can make allowance for the anatomical conditions of curved, conically shaped roots, with the prosthetic implant provision of the root canal—compared to methods of prior art—having a physiological character and being able to increase the strength of the root.

Flexible instruments are used for the mechanical drilling and the excavation of the root canal by hand in order to maintain the course of the root canal.

The excavation must not be effected with rotating instruments. Flexible instruments or tools may also be used that resection by translatory and pulling motions and provide a suitable shape.

The root post of the invention can serve not only as abutment for dental prosthetic constructions, but also for the filling of root canals. Moreover, the fixation part can jut out of the root apex into the jaw area, where it can provide for additional fixation of the dental root.

The drawing shows schematically, in longitudinal section, the fixation part of a root pin matched to a curved dental root. The fixation part (1) consists of four sections (2, 3, 4, 5) and is covered with a layer (6) made from porous, compressible material that establishes an intimate contact with the dental root (7). The section (2) located in the root post is the most ductile, the section located in the tip of the root apex having the greatest ductility or the least flexural rigidity and, toward the oral end of the fixation part, the material—continuously or in sections—is increasingly less ductile or increasingly more flexurally rigid.

From the viewpoint of tooth pin manufacture, it is most advantageous for the fixation part to consist of several assembled sections that have differing mechanical material properties, with the section in the root apex having the greatest ductility or the least flexural rigidity, and the sections toward the oral end of the fixation part being increasingly less ductile or increasingly more flexurally rigid.

Advantageously, the fixation parts consist of precious-metal alloys that, because of varying composition, thermal and/or mechanical treatment, have—continuously or in sections—differing ductilities or flexural rigidities.

Another advantage results by providing the surface of the fixation part with a layer made of a porous, compressible, biocompatible material. Fine gold or mixtures of fine gold with hydroxyapatite or tricalcium phosphate are especially suitable for this purpose.

Further variations and modifications of the foregoing will be apparent to those skilled in the art and are intended to be encompassed by the appended claims.

German priority application P 37 41 847.5-35 is relied on and incorporated herein by reference.

We claim:

1. A root post with a fixation part made of metallic material selected from a group consisting of precious-metal and base-metal alloys that can be inserted into the curved root canal of the root of a tooth, wherein the metallic material of the fixation part has mechanical properties that permit local adaption and fitting of the fixation part to a curved root canal, said fixation part in the longitudinal direction, has topically differing ductilities or flexural rigidities, the fixation part having a portion adapted for lying in the root tip and having the greatest ductility or the least flexural rigidity and said fixation part having a portion adapted for lying toward the oral end of the fixation part which is increasingly less ductile or increasingly more flexurally rigid.

2. The root post as set forth in claim 1, wherein the fixation part consists in the longitudinal direction of a plurality of assembled sections having differing mechanical material properties.

3. The root post as set forth in claim 1, wherein the fixation part consists of precious-metal alloys, which have differing ductilities or flexural rigidities.

4. The root post as set forth in claim 1, wherein the surface of the fixation part is provided with a layer of a porous, compressible, biocompatible material.

5. The root post as set forth in claim 4, wherein the layer is selected from a group which consists of fine gold and mixtures of fine gold with hydroxyapatite or tricalcium phosphate.

6. The root post as set forth in claim 1, which is adapted as an abutment for a dental prosthesis.

7. The root post as set forth in claim 1, which is adapted to fill root canals.

8. The root post as set forth in claim 1, which is adapted to have its tip just out of the root apex into the jawbone, where it ensures the fixation of the dental root.

* * * * *